(12) United States Patent
Cevette et al.

(10) Patent No.: US 9,564,059 B2
(45) Date of Patent: Feb. 7, 2017

(54) GALVANIC VESTIBULAR STIMULATION SYSTEM AND METHOD OF USE FOR SIMULATION, DIRECTIONAL CUEING, AND ALLEVIATING MOTION-RELATED SICKNESS

(71) Applicants: Mayo Foundation For Medical Education and Research, Rochester, MN (US); Vivonics, Inc., Bedford, MA (US)

(72) Inventors: Michael Cevette, Scottsdale, AZ (US); Jan Stepanek, Scottsdale, AZ (US); Anna Galea, Stow, MA (US)

(73) Assignees: Vivonics, Inc., Bedford, MA (US); Mayo Foundation For Medical Education and Research, Rochester, MN (US)

( * ) Notice: Subject to any disclaimer, the term of this patent is extended or adjusted under 35 U.S.C. 154(b) by 0 days.

(21) Appl. No.: 14/153,727

(22) Filed: Jan. 13, 2014

(65) Prior Publication Data
US 2014/0127666 A1    May 8, 2014

Related U.S. Application Data

(62) Division of application No. 12/660,768, filed on Mar. 4, 2010, now Pat. No. 8,718,796.
(Continued)

(51) Int. Cl.
*A61N 1/36* (2006.01)
*G09B 9/00* (2006.01)
(Continued)

(52) U.S. Cl.
CPC ................. *G09B 9/00* (2013.01); *A61N 1/323* (2013.01); *A61N 1/36014* (2013.01); *A61N 1/205* (2013.01)

(58) Field of Classification Search
CPC .. A61N 1/36032; A61B 5/1116; A61B 5/4863
See application file for complete search history.

(56) References Cited

U.S. PATENT DOCUMENTS

| 4,558,703 A | 12/1985 | Mark |
| 5,303,715 A * | 4/1994 | Nashner ............... A61B 5/1036 |
| | | 600/559 |

(Continued)

FOREIGN PATENT DOCUMENTS

| JP | 2004254790 | 9/2004 |
| JP | 2006288622 | 10/2006 |

(Continued)

OTHER PUBLICATIONS

Cress, et al., "An Introduction of a Direct Vestibular Display into a Virtual Environment", IEEE 1997, pp. 80-86.
(Continued)

*Primary Examiner* — Christopher D Koharski
*Assistant Examiner* — Natasha Patel
(74) *Attorney, Agent, or Firm* — Iandiorio Teska & Coleman, LLP

(57) ABSTRACT

The present invention relates to systems and techniques for stimulating a user. For example, materials and methods for manipulating nystagmus and the related vestibular system with coupling of galvanic vestibular stimulation (GVS) and visual cueing are provided herein. Use of GVS within the present invention may be applied to simulation, alleviating motion sickness, and directional cueing of a user to a precise target location.

12 Claims, 17 Drawing Sheets

Related U.S. Application Data

(60) Provisional application No. 61/209,262, filed on Mar. 5, 2009.

(51) Int. Cl.
 *A61N 1/32* (2006.01)
 *A61N 1/20* (2006.01)

(56) References Cited

U.S. PATENT DOCUMENTS

| | | | |
|---|---|---|---|
| 5,490,784 A | 2/1996 | Carmein | |
| 5,762,612 A | 6/1998 | Campbell | |
| 6,077,237 A | 6/2000 | Campbell et al. | |
| 6,219,578 B1* | 4/2001 | Collins | A61N 1/36032 607/2 |
| 6,443,913 B1* | 9/2002 | Kania | 600/595 |
| 6,497,649 B2 | 12/2002 | Parker et al. | |
| 6,546,291 B2 | 4/2003 | Merfeld et al. | |
| 6,748,275 B2 | 6/2004 | Lattner et al. | |
| 2002/0010497 A1* | 1/2002 | Merfeld et al. | 607/62 |
| 2004/0097839 A1 | 5/2004 | Epley | |
| 2007/0161875 A1 | 7/2007 | Epley | |
| 2007/0208403 A1* | 9/2007 | Della Santina et al. | 607/137 |
| 2009/0306741 A1* | 12/2009 | Hogle | A61N 1/36082 607/54 |

FOREIGN PATENT DOCUMENTS

| | | |
|---|---|---|
| JP | 2006288665 | 10/2006 |
| JP | 2007144057 | 6/2007 |
| JP | 2008225245 | 9/2008 |
| JP | 2013509227 | 3/2013 |

OTHER PUBLICATIONS

Hoffmann, Leah. "Remote-Controlled Humans," http://www.forbes.com/2005/08/04/technology-remote-control-humans_cx_lh_0804remotehuman_print.html, Aug. 4, 2005 (one (1) page).

Knight, Will. "Remote-controlled humans enhance immersive games," http://www.newscientist.com/article/dn7829-remotecontrolled-humans-enhance-immersive-games.html, Aug. 10, 2005 (two (2) pages.

Written Opinion of the International Searching Authority, mailed Oct. 7, 2010, in International Application No. PCT/US2010/000657, 7 pages (unnumbered).

* cited by examiner

GALVANIC VESTIBULAR STIMULATION SYSTEM AND METHOD OF USE FOR SIMULATION, DIRECTIONAL CUEING, AND ALLEVIATING MOTION-RELATED SICKNESS

RELATED APPLICATIONS

This application is a divisional application which claims the benefit of and priority to U.S. patent application Ser. No. 12/660,768 filed on Mar. 4, 2010, which claims the benefit of and priority to U.S. Provisional Application Ser. No. 61/209,262 filed on Mar. 5, 2009 under 35 U.S.C. §§119, 120, 363, 365, and 37 C.F.R. §1.55 and §1.78.

GOVERNMENT RIGHTS

This invention was made with government support under Nos. N00014-06-M-0209, N68335-07-C-0443, and N68335-08-C-0294 awarded by the Navy. The government has certain rights in the invention.

FIELD OF THE INVENTION

The present invention relates to systems and techniques for simulating motion to a human subject, alleviating motion sickness, and directional cueing and more particularly, relates to manipulating nystagmus and the related vestibular system with coupling of galvanic vestibular stimulation (GVS).

BACKGROUND OF THE INVENTION

Acceleration of the head evokes responses from the vestibular receptors in order to compensate for head motion. This is referred to as the vestibular ocular reflex (VOR). Under normal conditions, the VOR can allow an individual to maintain visual fixation during head movement, by ensuring that for every movement of the head, there is an equal and opposite compensatory movement of the eyes. Stimulation of the vestibular receptors in the semi-circular canals can result from angular head acceleration and from stimulation of the otolith organs from linear acceleration (i.e. gravity, head tilt, and centrifugal force). These signals can activate the central nervous system through reflexes that evoke changes in the extra-ocular muscles, the visual system, and posture, enhancing acuity during head rotation and balance during changes in body position. The semicircular canals, and the signals they send to the brain, function as yoked pairs. In the absence of head motion, a train of pulses is sent from each side of the head. As the head experiences acceleration (other than gravity), the pulse train on one side of the head increases in frequency while on the other side it decreases. Our brains have adapted to interpret this differential signal as acceleration. When the central nervous system cannot balance the excitatory and inhibitory inputs from the semi-circular canals and otolith organs, the individual can experience an illusion of motion and/or loss of balance.

There has been various research into the use of galvanic vestibular stimulation in terms of simulators, directional cueing, and alleviating symptoms of motion sickness, however, there are still many needed improvements to the current technology. In particular, there is a need for a simulator system that gives a user a more realistic view of driving a vehicle such as a boat, airplane, automobile, and the like. For example, even flight simulators that use a motion platform are limited in the amount and type of motions they can impart to the user. There has also been some work in the use of GVS to alleviate feelings of motion sickness. However, the current systems use AC current to override the natural brain signals that cause a person to feel sick. This overriding requires more electrical energy being provided to a user. The use of more electrical energy can be a safety concern to a user. Therefore, there is a need for GVS technology that uses less external electrical energy on a person. Additionally, GVS technology has been applied to users causing them to physically move side to side. However, there is a need to develop this technology to be more precise and accurate as well as be able to move a person in many different directions, including forward and backward. For example, it would be advantageous to the public to be able to precisely direct a person or a group of people to a specific distinct location with the use of GVS technology.

SUMMARY OF THE INVENTION

The present invention relates to systems and techniques for a stimulation process. For example, materials and methods for manipulating nystagmus and the related vestibular system with coupling of galvanic vestibular stimulation (GVS), orientation sensors, and visual inputs are provided. For example, materials and methods for simulating rotational movement (e.g., roll, pitch and yaw) are provided. For example, methods featuring a combination of stimulations for isolating perceived rotations and directions are provided. For example, a galvanic vestibular stimulator featuring surface electrodes, and methods for enhancing and mitigating motion perception are provided.

Such use of GVS may be employed in a variety of environments where the GVS is used to accentuate or decrease motion that is otherwise experienced by a human subject—to attempt to match (or perhaps even mismatch) ocular clues and vestibular clues for the subject. For example, a subject who is perceiving motion in a flight simulator—whether from moving images projected by the simulator or actual motion of a set or other platform on which the subject is mounted—may sometimes suffer from simulator sickness. GVS may be used to decrease both the incidence and severity of nausea and dizziness that a subject might otherwise experience in such a situation (sometimes known as "simulator sickness"), and thus permit more rewarding and lengthier training. The present invention could also allow subjects to avoid limitations on flying immediately following a simulator training session due to motion sickness. Therefore, the present invention would allow for a subject to go through a simulator training session without getting sick and then fly the real mission immediately after the simulator. This enables the most recent information to be used in the creation of the mission simulation. Similarly, electronic GVS may be coordinated with motion sensed in an actual vehicle such as an airplane, to decrease the incidence and severity of motion sickness. GVS may also be used to augment a subject's other perceptions of motion, such as in a professional flight simulator or video game, where a game controller may provide inputs about the subject's motion in the game to a GVS controller, which may in turn provide stimulation to the subject so that the subject perceives physical motion that matches, at least to some extent, the visual motion they are seeing on their screen or screens.

The GVS system may be exemplified as a motion simulation system having a computer receiving inputs corresponding to a sensed motion experienced by a subject. The system also includes an electronic stimulation determination module that is connected to the computer for determining a level of electrical stimulation to be provided to the human subject to create non-visual perceived motion in the subject corresponding with the motion experienced by the subject as received by the computer. Also, the system has an electrical stimulator connected to the electronic stimulation determination module for generating electrical signals through the electrodes to create in the subject a sensation of motion matched to the sensed motion experienced by the human subject. The system further includes at least three distinct sets of electrodes connected to the electrical stimulator. The electrodes are located on the human subject. Stimulation passes between at least two electrodes of each distinct set. These three distinct sets of electrodes may preferably include an electrode on the subject's forehead, an electrode on the subject's mastoid, an electrode on the subject's alternative mastoid, and an electrode on the subject's back of the neck.

There is also a computer-implemented method of simulating motion in a subject's perception which includes receiving an indication of a sensed motion experienced by the subject, determining a level of motion-related stimulation needed to match the subject's response to the sensed motion experienced by the subject, and delivering electrical signals to at least three distinct sets of electrodes placed in contact with the subject to provide the subject with a non-visual perception of motion in at least three separate directions that are coordinated with the sensed motion experienced by the subject.

A computer-implemented method of providing directional cueing includes receiving an indication of the direction and speed of the motion of a human subject, determining the course needed to direct the subject to a desired location. The course includes one or more movements needed to move the subject to the desired location. Another step in the process is determining a level of stimulation needed to suggest to the subject the movements needed to achieve the course to the desired location. The level of stimulation correlates with a desired direction and speed that is input for each needed movement within the course. The method further includes delivering electrical signals to at least two distinct sets of electrodes placed in contact with the human subject to cause the subject to move along the course to the desired location.

There is also a system for providing directional cueing including a computer that receives motion inputs corresponding to a location and movement of a human subject. The motion input includes a measurement of direction and speed. The system also has an electronic stimulation determination module connected to the computer for determining a level of electrical stimulation to be provided to the subject in order to direct the subject on a course to a desired location. This course includes one or more direction and speed components. The system further includes an electrical stimulator connected to the electronic stimulation determination module for generating electrical signals to cause the subject to move in one or more directions and at a speed matching the course to the desired location. The subject stimulator stops generating electrical signals when the subject reaches the desired location. There are also at least two distinct sets of electrodes connected to the electrical stimulator. These electrodes are located on the human subject causing stimulation from the electronic stimulator to pass between at least two electrodes of each distinct set.

Unless otherwise defined, all technical and scientific terms used herein have the same meaning as commonly understood by one of ordinary skill in the art to which this invention pertains. Although systems and techniques similar or equivalent to those described herein can be used to practice the invention, suitable systems and techniques are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments are set forth in the accompanying drawings and the description below. Other features, objects, and advantages will be apparent from the description and drawings, and from the claims.

BRIEF DESCRIPTION OF THE DRAWINGS

FIG. 4A is the plot of eye velocity without GVS (no electric stimulation). FIG. 4B is the plot of eye velocity with simultaneous GVS.

DETAILED DESCRIPTION OF THE INVENTION

This document relates to systems and techniques for a stimulation system. For example, materials and methods for manipulating nystagmus and the related vestibular system with coupling of galvanic vestibular stimulation (GVS), accelerometers, and visual inputs are provided. For example, battery operated galvanic vestibular stimulators featuring surface electrodes, and methods for simulating motion in a subject are provided.

GVS systems and methods described herein can be used to affect motion cues. Motions involved in the present systems and methods may be linear, rotational and a combination of linear and rotational. Linear motions are movement vertically, forward/backward, and left/right. Rotational motions include a yaw angle, pitch angle, and roll angle. Yaw is rotation about the z-axis, pitch is rotation about the y-axis, and roll is rotation about the x-axis. For example, a GVS system described herein can be used to simulate the right roll to about 90 degrees or greater, left roll to about 90 degrees or greater, positive pitch to about 90 degrees or greater, negative pitch to about 90 degrees or greater, right yaw to about 360 degrees or greater, and left yaw to about 360 degrees or greater. In some cases, pure pitch, roll, and yaw can be simulated. In some cases, a combination of pitch, roll, and yaw can be simulated. In some cases, the materials and methods described herein can enhance a subject's sensation of motion in combination with actual motion. For example, enhanced perception of rotational acceleration can be stimulated while a subject is rotating in a rotational chair. In some cases, the materials and methods described herein can be used to mitigate spatial disorientation. For example, a diminished sensation of motion can be stimulated. In some cases, the materials and methods described herein can be used to create spatial disorientation in a simulator for training purposes. In some cases, the materials and methods described herein can be used to mitigate motion sickness or simulator sickness. In some cases, the materials and methods described herein can be used for directional cueing. For example, sensations associated with turning or stopping can be provided to an ambulatory subject.

Figure 1A:
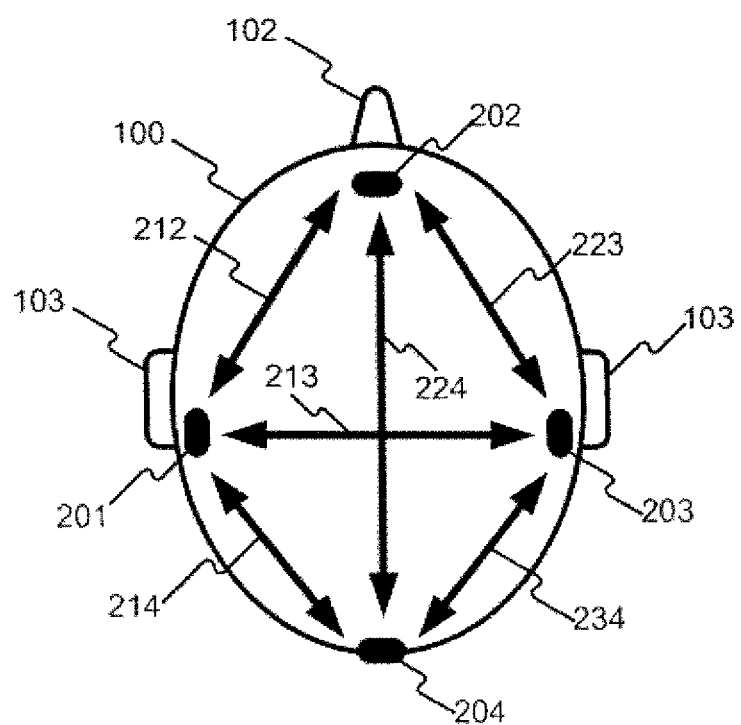
FIG. 1A is a depiction of the electrode placement for various stimulation embodiments of the present invention as shown from the top of the subject's head.

GVS systems and methods described herein include at least two electrodes for stimulating a subject's vestibular system. Two or more electrodes may also be used. FIG. 1A depicts a group of possible embodiments of the present invention with a top view of a subject's head 100 showing the nose 102 and ears 103 with four active electrodes. The four possible active electrodes in FIG. 1 are positioned: at the subject's left mastoid 201, at the subject's forehead 202, at the subject's neck 203 and at the subject's neck 204. The direction of stimulation between each set of electrodes is indicated: between the electrodes at the left mastoid and forehead (212), between the electrodes at the forehead and right mastoid (223), between the electrodes at the left and right mastoid (213), between the electrodes at the right mastoid and the neck (234), between the electrodes at the left mastoid and neck (214), and between the electrodes at the forehead and the neck (224). Other electrode arrangements may also be made.

For example, a GVS system described herein can have one electrode attached on the forehead, one electrode on the left high mastoid, one electrode on the left low mastoid, and one on the nape of neck. In some cases, a GVS system described herein can have one electrode on the right high mastoid, one electrode on the right low mastoid, one electrode on the left high mastoid, and one electrode on the left low mastoid. In some cases, a GVS system can include a grounding electrode, which can be placed at any suitable position for safety, such as the nape of the neck, for example. In some cases, a GVS system can feature electrodes integrated into a device, such as a headband or helmet.

Figure 1B:
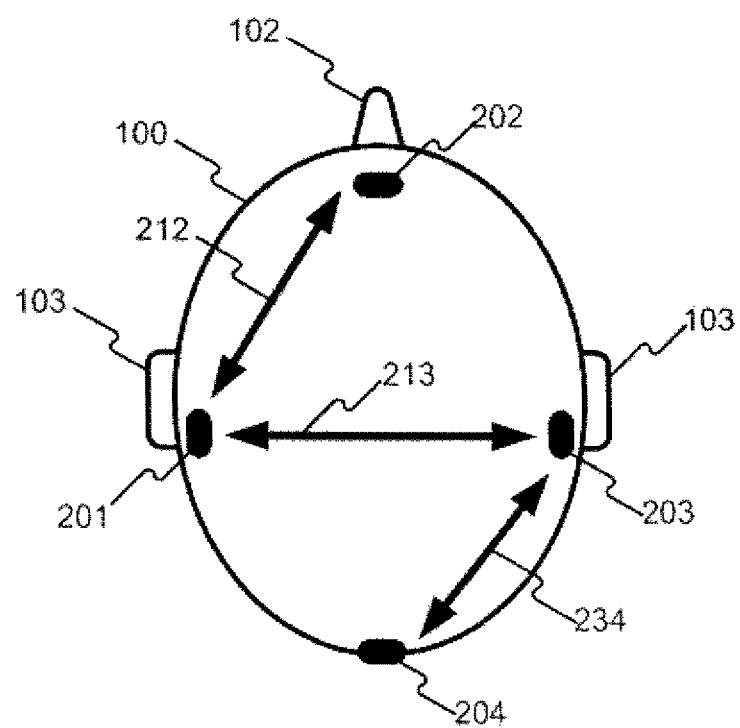
FIGS. 1B and 1C are depictions of two embodiments of the present invention including electrodes used in three distinct sets.
Figure 1C:
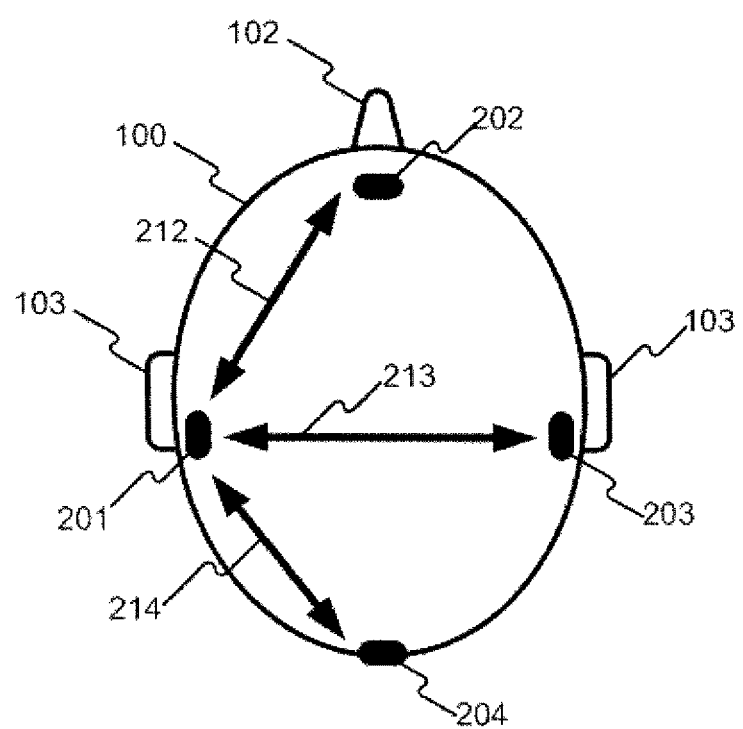
Figure 1D:
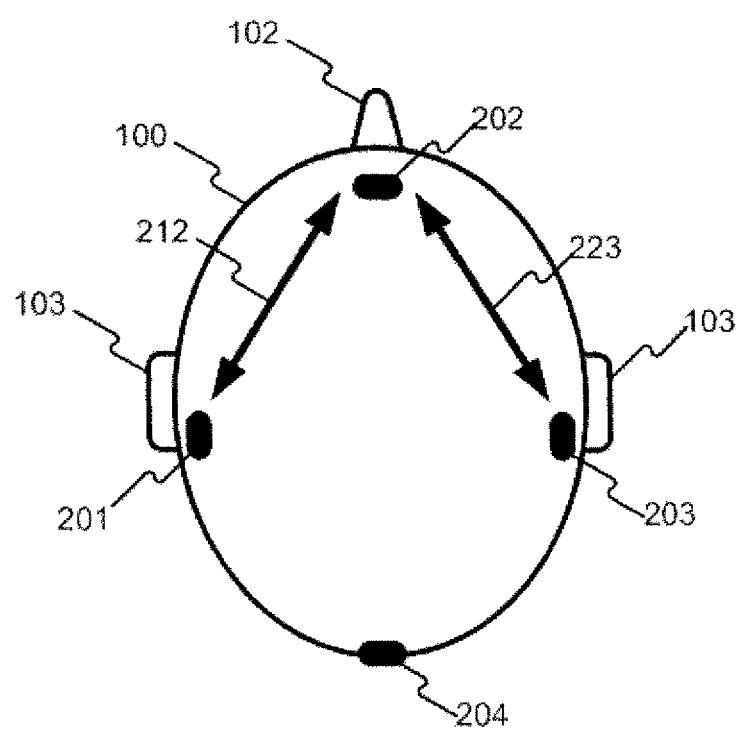
FIG. 1D is a depiction of two non-distinct sets of electrodes.

The embodiments of the present simulator may include at least two distinct sets of active electrodes more preferably three or more distinct sets of active electrodes. For example in FIG. 1B, a first set may be a forehead electrode to the left mastoid electrode (212), a second set may be the left mastoid electrode to the right mastoid electrode (213), and a third set may be the right mastoid electrode to a neck electrode (234). For example in FIG. 1C, a first set may be a forehead electrode to the left mastoid electrode (212), a second set may be the left mastoid electrode to the right mastoid electrode (213), and a third set may be the left mastoid electrode to a neck electrode (214). In FIG. 1D, the electrode set of the forehead and left mastoid (212) and the electrode set of the forehead and right mastoid (223) are symmetrical and not considered distinct. FIG. 1D displays a subject using a GVS system that results in only one distinct set of electrodes. The stimulation between symmetrical sets 212 and 223 results in simulated motion in the same plane, therefore, the electrode sets 201-202 and 202-203 are not considered distinct from one another.

Figure 2A:
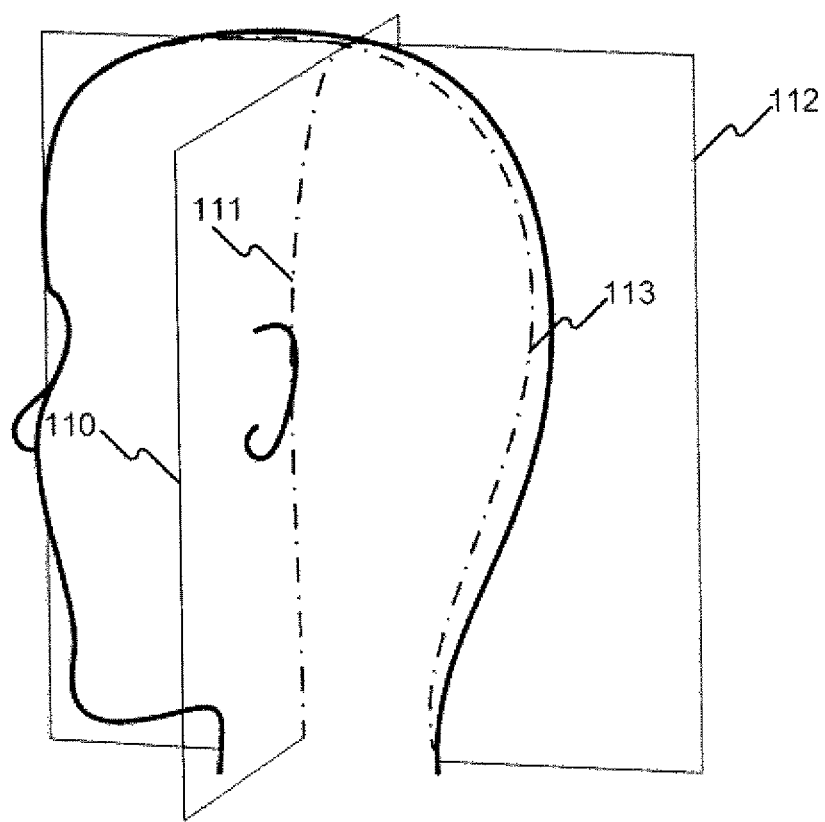
FIG. 2A is a three dimensional view of the coronal 110 and sagittal 112 planes intersecting the head.
Figure 2B:
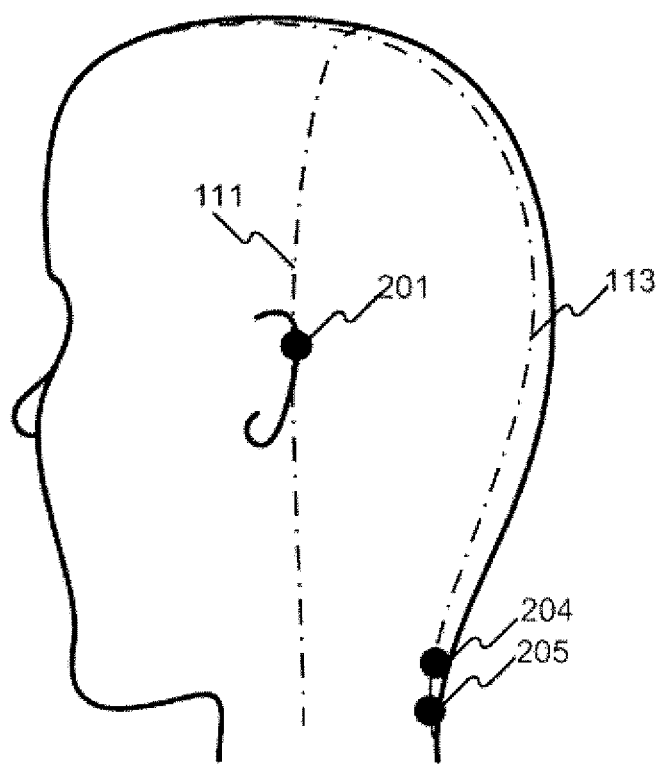
FIGS. 2B and 2C are depictions of electrodes 201, 202, 203, 204, and a neutral electrode 205 placed on the coronal 111 and sagittal 113 lines.
Figure 2C:
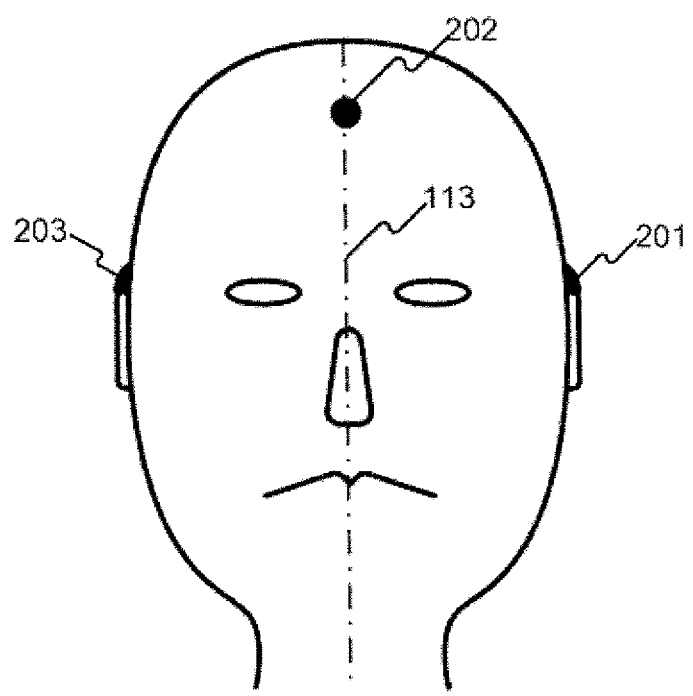

The present invention is further exemplified within the embodiments shown in FIGS. 2A-2C. An isometric view of a subject's head is shown in FIG. 2A showing the sagittal plane 112 and coronal plane 110 bisecting a user's head. The lines of the planes bisecting the user's head are shown as the sagittal line 113 and the coronal line 111. In FIGS. 2B and 2C, one embodiment includes a subject's head with electrode 201 positioned at the subject's left high mastoid along the coronal line 111, electrode 203 positioned at the subject's right high mastoid along the coronal line 111, electrode 202 positioned at the subject's forehead along the sagittal line 113, and electrode 204 and neutral electrode 205 are positioned at the subject's nape of neck along the sagittal line 113.

Simulation of motion in roll, pitch, and yaw can be accomplished by directional stimulation between electrode sets or a combination of electrode sets. All relevant electrodes may be stimulated simultaneously in order to achieve simulation of motion. Directional stimulation allows for stimulation to pass in either direction between two electrodes within a set. In order for stimulation to pass in one direction or another, a first electrode within a set is commanded to absorb current (anode) while a second electrode within the set is commanded to emit current (cathode). Therefore, stimulation will directionally flow from the second electrode to the first electrode. For example, a motion that is mainly roll left may be simulated by stimulating electrodes at the right mastoid (anode) and the nape of the neck (cathode) causing current to flow in the direction from the neck to the right mastoid. For example, a motion that is mainly a roll right and pitch backward may be simulated by stimulating electrodes at the forehead (anode) and the right high mastoid (cathode) causing current to flow in the direction from the right high mastoid towards the forehead. For example, a motion that is mainly yaw right can be simulated by stimulating electrodes at the right high mastoid (anode) and left high mastoid (cathode) causing current to flow in the direction from left high mastoid to right high mastoid. In some cases, pure pitch can be simulated by using a combination of stimulations, such as by stimulating electrodes at the forehead and the right mastoid (roll left and pitch forward), in combination with stimulating electrodes at the left high mastoid and the nape of the neck (roll right).

GVS systems and methods described herein may use AC current or preferably near DC current and use a maximum stimulation of about 2.5 mA. In some cases, a stimulation dose can be from about 1 mA to about 2.5 mA. For example, a stimulation dose can be about 1, 1.5, 2.0, and 2.5 mA. In some cases, maximum stimulation can be applied without any time delay and with greater than 2.5 mA of current. In some cases, stimulation can be ramped up to the maximum stimulation current over a period of time. For example, stimulation can be ramped up from about 0 ms to about 600 msec. For example, stimulation can be ramped up in about 25, 75, 175, 300, or 600 msec. In some cases, stimulation can be terminated immediately after the response has been achieved. In some cases, stimulation can be ramped down. For example, stimulation can be ramped down from about 0 ms to about 600 msec. For example, stimulation can be ramped down over 25, 75, 175, 300, or 600 msec.

Figure 3:
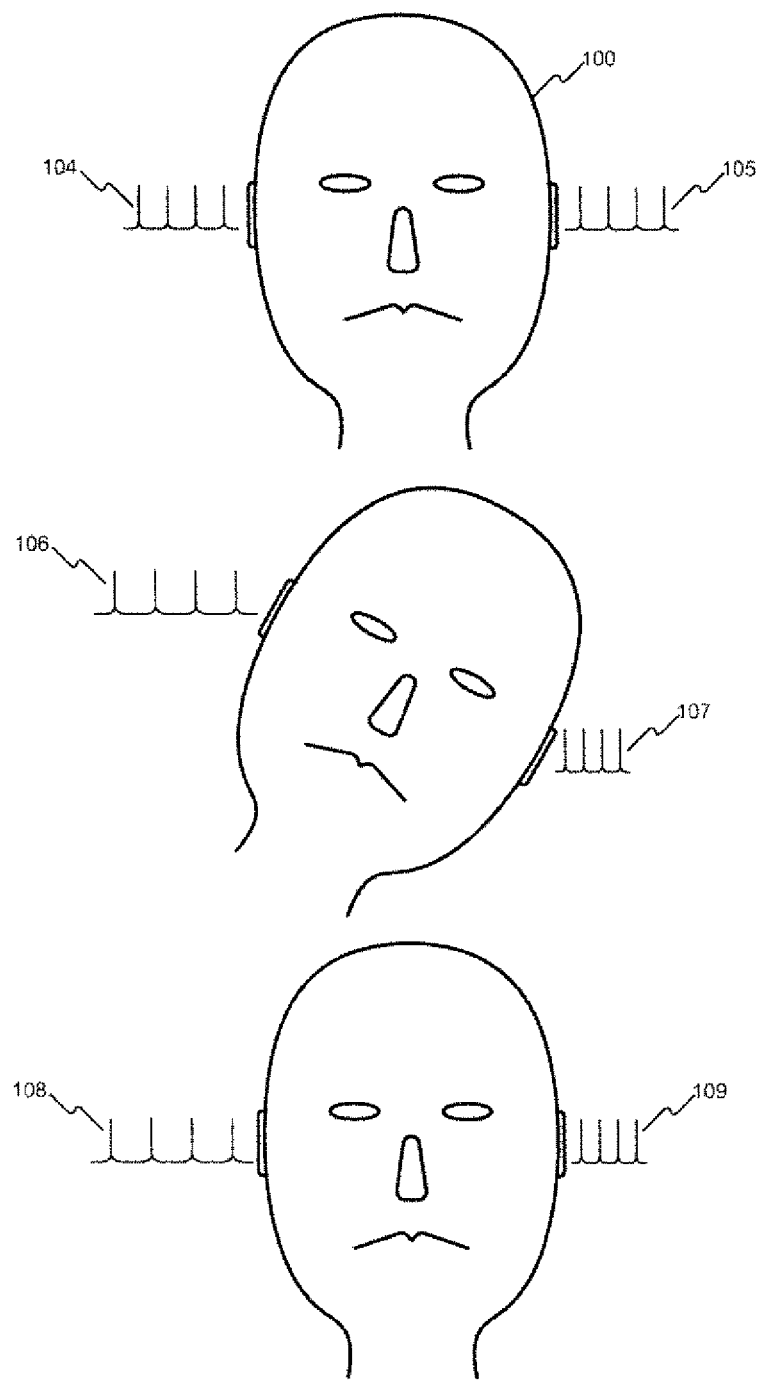
FIG. 3 is a depiction of perceived motion in response to directed stimulation of electrode sets.

In one embodiment, a low-level DC signal may be used which may be positive at one stimulation point and negative at another stimulation point on the head to naturally alter the train of pulses. The positive signal serves to depolarize the cells causing a decrease in their effective latency period, while the negative signal has the opposite effect. Current-limited stimulation may be used, whereas the maximum current between any set of electrodes is kept at 2.5 mA for certain implementations. For example, FIG. 3 shows examples of a human subject 100 in three different states, with vestibular activation patterns superimposed over each state. The first state shows equilibrium for the subject, with equal activation levels on both sides of the head (104, 105), while the second state shows the natural vestibular activation signals induced in the subject when they tilt their head (106, 107). The third state shows a perception of tilt or motion that is induced in the subject by unequal GVS stimulation at two different points on the head. This third state may be induced with any variation of electrode sets as shown in FIGS. 1A-C while preferably having at least 3 distinct sets. The vestibular signals in the third state (108, 109) are similar to those in the second state (106, 107). In the second state (head tilt), train of pulses on one side of the subject's head slow down while the train of pulses speed up on the other side. In order to change the train of pulses, stimulations include an increase/decrease of voltage and current applied to the subject. By increasing/decreasing voltage and current, the train of pulses can be sped up or slowed down to match a specific movement. In the third state, both voltage and current were applied unequally at two different points on the subject's head causing a change in the vestibular signal from equilibrium (104, 105) to a third state (108, 109). Therefore, the application of GVS (third state) induced this same effect to the subject without tilting the head.

Feedback mechanisms from the subject can also be combined with other mechanisms discussed here. For example, a subject can be subjected to visual motion (e.g., via a simulator or videogame background being displayed in motion before the subject), perceived motion (e.g., via GVS stimulation), and real non-visual motion (e.g., via a seat or other platform such as a vehicle on which the subject is positioned), or any combination of the three. The subject may provide feedback regarding their total perception of motion using a joystick. In addition, the subject may be provided with additional input mechanisms such as joysticks to control the level of perceived motion, such as a control stick for a simulator or a D-pad for a videogame, and they could alternatively or simultaneously provide input on a different joystick regarding the level of perceived motion that they created by their own input to the simulator or video game system.

The invention will be further described in the following examples, which do not limit the scope of the invention described in the claims.

EXAMPLES

Example 1

Enhancing Motion Perception Using Vestibular Stimulation

Electrodes were attached to the subject, as shown in FIGS. 2B and 2C. As shown in FIGS. 2A-C, electrodes may be placed along the sagittal and coronal planes (112 and 110 respectively). Placement along the sagittal and coronal planes allows for more accurate/precise inducement of perceived motion on a subject. Along the coronal plane line 111, one or more electrodes may be placed along the mastoid. Along the sagittal plane line 113, one or more electrodes may be placed on the centerline of the forehead or on the back of the neck. Electrodes may be positioned as follows: one electrode on left high mastoid 201, forehead 202, right high mastoid 203 and nape of neck 204. A grounding electrode (neutral) 205 may be positioned on the neck. The grounding electrode 205 is not active and is present as a safety precaution for absorbing any leftover current in a subject's head.

Figure 4A:
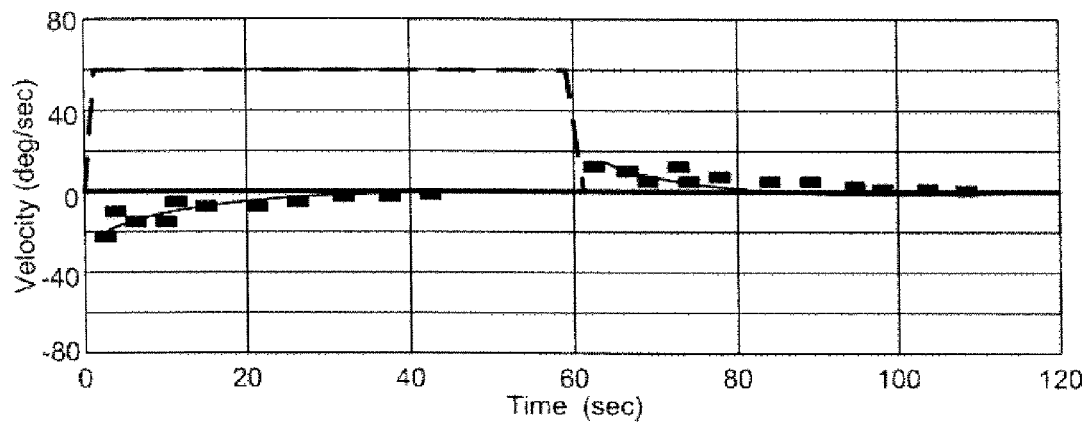
FIGS. 4A and 4B are plots of eye velocity (degrees/second) over time representing nystagmus due to subject rotation.
Figure 4B:
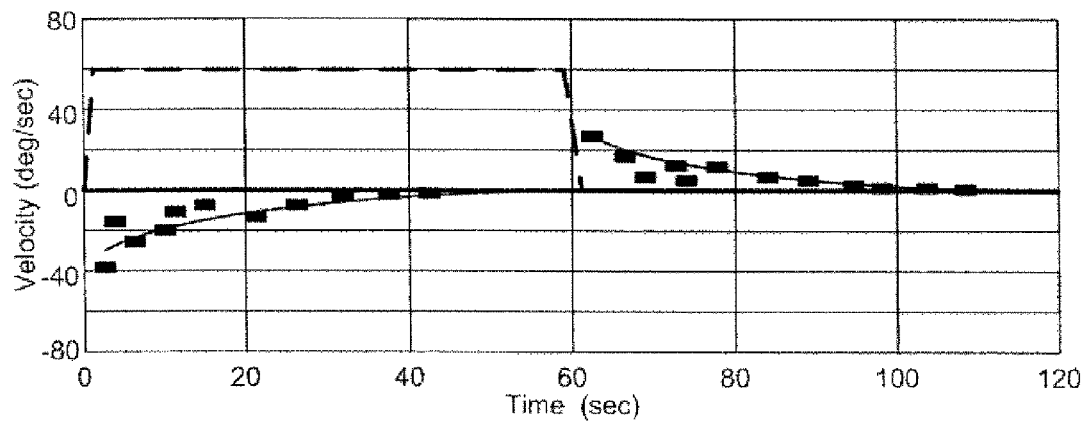

In a first test, a subject was seated in a rotary chair and rotated at a fixed velocity (first to one side and then to the other) without any electrical stimulation. Nystagmus was determined by monitoring eye velocity. In the second test, the subject was once again rotated but with an added vestibular stimulation of motion in the yaw direction (simulate yaw) by stimulating electrode sets as shown in FIG. 1B. The yaw direction is the same as spinning in a rotary chair which is turning about the vertical axis. Stimulating a subject in a yaw direction amplifies the actual movement in the rotary chair. FIGS. 4A and 4B display plots of eye velocity (degrees/second) over time representing nystagmus due to subject rotation. The dashed line in these figures represents chair velocity. In FIG. 4A, there was no electric stimulation used on the subject while being rotated in the chair. FIG. 4B displays the impact to a subject's eye velocity with added GVS stimulation. The comparison of these graphs describes the impact that vestibular stimulation can have on a subject's sensation of motion. In FIG. 4B and Table 1, the results show enhanced eye velocity consistent with the greater perceived rotational speed. These results demonstrate enhanced sensation of motion with GVS.

TABLE 1

| Chair | Eye velocity (degrees/second) | | |
| --- | --- | --- | --- |
| angular velocity (degrees/ second) | Without GVS | With GVS = 2.5 mA * sign (chair_speed) | Percentage increase due to vestibular stimulation |
| 60 | 21 | 29 | 38% |
| −60 | 16 | 22 | 38% |

Example 2

Stimulation Ramps

The stimulation methods described in this example may be based on near-DC values. Achieving the desired stimulation level can be accomplished in a number of ways, including with ramp-ups and ramp-downs. Table 2 summarizes example stimulation scripts tested. Data was collected from 7 subjects as described above, except that stimulations included different ramp-up or ramp-up and ramp-down times.

TABLE 2

| Ramp-up stimulation | Ramp-up and Ramp-down stimulation |
|---|---|
| 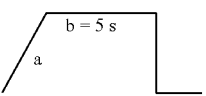 | 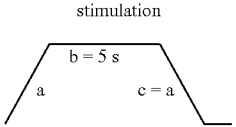 |
| Values for 'a' | Values for 'a' and 'c' |
| 0 ms | 0 ms |
| 25 ms | 25 ms |
| 75 ms | 75 ms |

TABLE 2-continued

| Ramp-up stimulation | Ramp-up and Ramp-down stimulation |
|---|---|
| 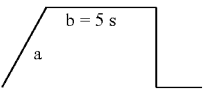 | 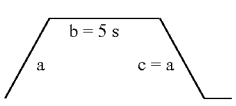 |
| Values for 'a' | Values for 'a' and 'c' |
| 175 ms | 175 ms |
| 300 ms | 300 ms |
| 600 ms | 600 ms |

Figure 5:
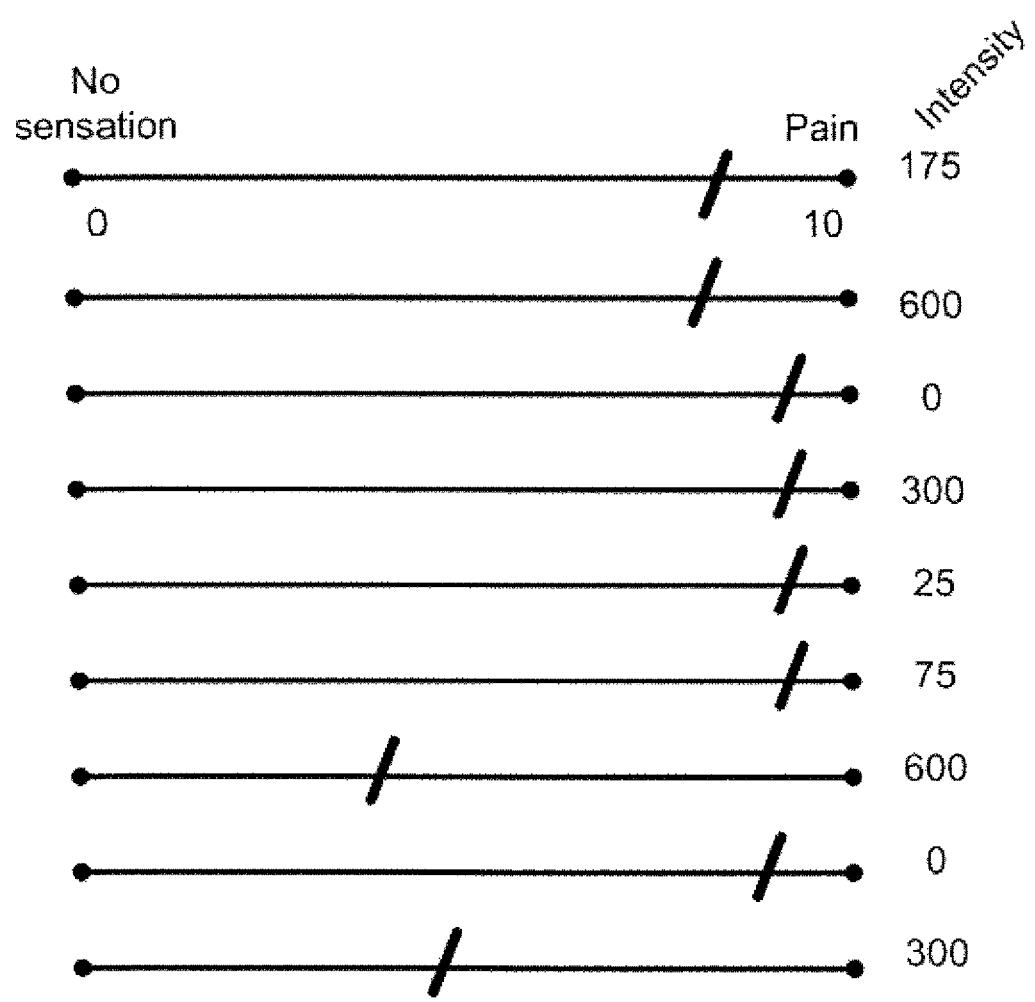
FIG. 5 is a depiction of an example subject's response to ramp stimulation protocol displayed in visual analog scales.
Figure 6:
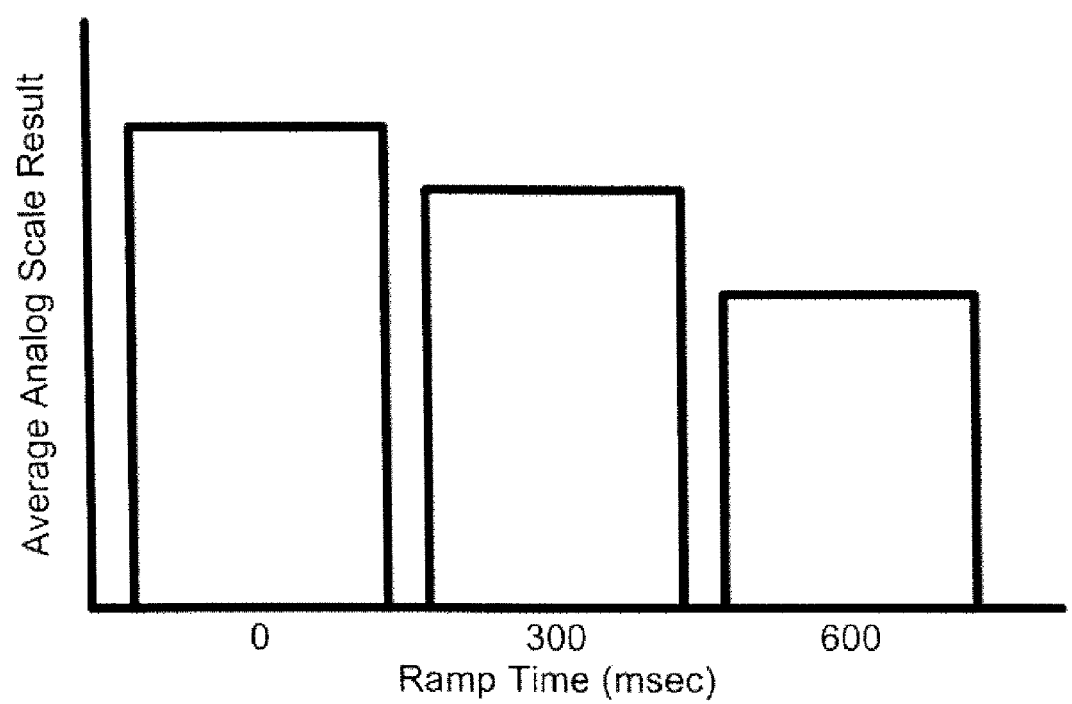
FIG. 6 is a plot of averaged recorded values from a group of subjects' visual analog scales versus ramp-up time at 0, 300, and 600 msec.

FIG. 5 shows a typical response to the ramp stimulation protocol displayed in visual analog scales. FIG. 6 shows data for all 7 subjects (plots averaged recorded values from subjects' visual analog scales versus ramp-up times). This data indicates that the sensation at the skin decreased with longer ramp-up times with some variability between subjects.

Example 3

Dose Response Tests

Data Collection

Subjects were seated in a rotary chair with electrode placement as indicated above. Current was applied simultaneously to positive and negative electrodes within each set, without visual input required, to induce a feeling of a desired rotation. To quantify the dose response in all three axes of rotation, each subject underwent thirty protocols lasting 20 seconds. The protocols utilized ten different combinations of electrode stimulation sets (Table 3) to quantify the dose response in all three axes of rotation. Prior to testing, the script order was randomized for each subject. Perception data was collected from each subject via an avatar program. Subjects were provided with a wireless joystick for reporting sensed motion. Data was collected from 21 subjects.

TABLE 3

| Perceived Motion | Test Group 1: ±1.5 mA | | | Test Group 2: ±2.0 mA | | | Test Group 3: ±2.5 mA | | |
|---|---|---|---|---|---|---|---|---|---|
| | Script No. | Positive Electrode | Negative Electrode | Script No. | Positive Electrode | Negative Electrode | Script No. | Positive Electrode | Negative Electrode |
| Roll right Pitch backward | 1 | #201 | #202 | 11 | #201 | #202 | 21 | #201 | #202 |
| Roll right Pitch forward | 2 | #202 | #201 | 12 | #202 | #201 | 22 | #202 | #201 |
| Roll right Pitch backward | 3 | #202 | #203 | 13 | #202 | #203 | 23 | #202 | #203 |
| Roll left Pitch forward | 4 | #203 | #202 | 14 | #203 | #202 | 24 | #203 | #202 |
| Roll left | 5 | #203 | #204 | 15 | #203 | #204 | 25 | #203 | #204 |
| Roll right | 6 | #204 | #203 | 16 | #204 | #203 | 26 | #204 | #203 |
| Roll right | 7 | #204 | #201 | 17 | #204 | #201 | 27 | #204 | #201 |
| Roll left | 8 | #201 | #204 | 18 | #201 | #204 | 28 | #201 | #204 |
| Yaw left | 9 | #201 | #203 | 19 | #201 | #203 | 29 | #201 | #203 |
| Yaw right | 10 | #203 | #201 | 20 | #203 | #201 | 30 | #203 | #201 |

Figure 7:
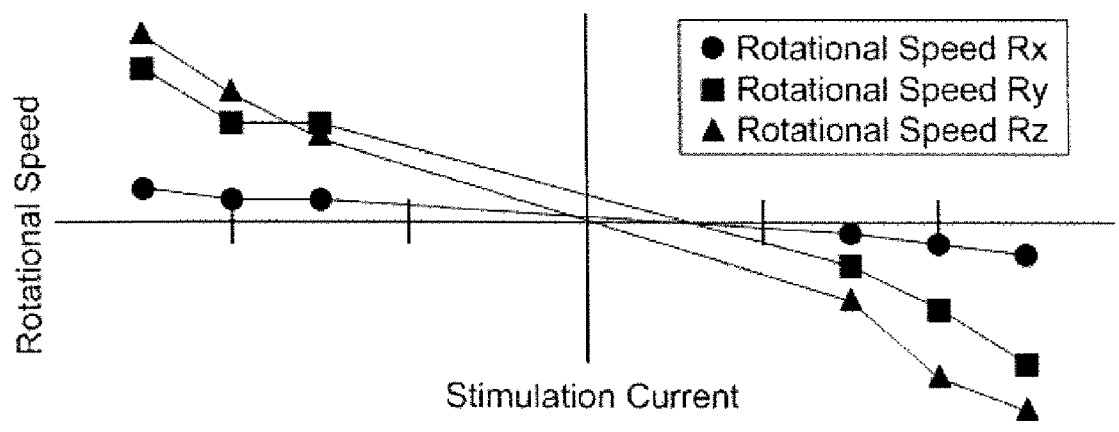
FIG. 7 is a representative plot showing relationship between stimulation current (mA) between one set of electrodes and perceived rotations about each axis.

Data was recorded as the three inclination angles of the avatar about the x-axis (pitch, reported as ±180 degrees), y-axis (roll, reported as ±90 degrees), and z-axis (yaw, reported as ±180 degrees) respectively. FIG. 7 shows a typical plot of the data obtained from the dose-response test. Each curve represents the perceived rotations between electrodes 201 and 203 for each axis (x, y, z) over a stimulation period of 20 seconds. There was very little perceived rotation about the x-axis in this example, but quite a bit about each of the y- and z-axes for this stimulation. In all cases, the perceived rotation (R) was zero for no stimulation (S). A basic relationship between the perceived rotations about the three axes ($R_x$, $R_y$, and $R_z$) and the directions of stimulation was obtained by performing a curve fit through these data plots. In one embodiment (for example FIG. IC), electrodes are numbered 1 through 4 and the electrode sets are labeled $S_{12}$, $S_{13}$, and $S_{14}$. Electrode 1 is 201, electrode 2 is 202, electrode 3 is 203, and electrode 4 is 204 as shown in the figures. By placing a higher voltage at electrode 1 compared with electrode 2, it causes current to flow from electrode 1 to electrode 2. This creates a positive $S_{12}$. However, other embodiments that include other combinations of electrodes may be possible such as $S_{23}$, $S_{13}$, $S_{14}$, $S_{12}$, $S_{31}$, $S_{14}$, and so forth.

Stimulation from electrode 2 to 3 resulted in an equal but opposite effect to stimulation from electrode 2 to 1. Conversely, stimulation from electrode 3 to 2 resulted in an equal effect to stimulation from electrode 2 to 1. Results of stimulation from electrode 3 to 2 and from 2 to 1 were averaged ($S_{321}$, stimulation either from electrode 3 to 2 or from 2 to 1). The situation was identical for stimulations from 1 to 4 and from 4 to 3, so data was collected into a single value $S_{143}$.

During testing and to maintain a control, some subjects may be stimulated with GVS while other subjects were not stimulated with GVS. Stimulated subjects may experience a localized sensation such as slight tingling or potentially mild tingling. Thus, non-stimulated subjects may be given a small "sham" stimulation, e.g., 1 mA current applied bilaterally such as behind the ears, so as to make the subject believe that they are receiving GVS.

Data Analysis

A set of three equations can be used to describe the relationship of inputs (S) to output rotations (R): Rotation in x, y, or z (roll, pitch, and yaw) is given by:

$$R_x = AS_{13} + BS_{321} + CS_{143}$$

$$R_y = DS_{13} + ES_{321} + FS_{143} \quad R = f(S)$$

$$R_z = GS_{13} + HS_{321} + IS_{143}$$

Note that in these equations, the values R are for perceived rotations which may be in degrees/second, radians per hour, or the like and the values S are stimulations in milliamps (mA), Amps, or the like. Each letter (A through I) represents a time-varying value in the matrix that relates input S to output R. For subjects looking forward, the perceived rotation was in line with simulator axes. For a subject looking elsewhere, the relative orientation of the simulator can be assessed using a tilt tracker and multiplying or otherwise mathematically removing the actual orientation by the three desired rotations. Relating S to desired Rs enabled the formation of the equations:

$$S_{13} = A'R_x + B'R_y + C'R_z$$

$$S_{321} = D'R_x + E'R_y + F'R_z \quad S = f'(R)$$

$$S_{143} = G'R_x + H'R_y + I'R_z$$

In conclusion, the three equations that show the required stimulations S as a function of the desired rotations R are the inputs needed in order to drive vestibular stimulation within a motion simulation system. Therefore, a desired motion (input) can be achieved by running stimulation software embedded with these three equations in order to command stimulation of electrode sets in a specific pattern relative to the equations' outputs.

There are also other embodiments of the present invention allowing for more than 3 motions up to as many as 6 motions. These other motions are possible with additional equations. For example, Roll, Pitch, Yaw, Vertical, Forward/Backward, and Left/Right can be achieved as:

$$\begin{bmatrix} S_A \\ S_B \\ S_C \\ S_D \\ S_E \\ S_F \end{bmatrix} = M' \begin{bmatrix} R_X \\ R_Y \\ R_Z \\ D_V \\ D_F \\ D_L \end{bmatrix}$$

The M' is the inverse of the 6×6 matrix that maps the 6 directions of stimulation onto the six motions. Roll, pitch, and yaw are rotational directions and vertical (up and down), forward/back, and left/right are linear directions. This adds up to 3 potential rotational directions and 3 potential linear directions. The rotational directions are labeled with R (Rx, $R_Y$, and $R_Z$). The linear directions are labeled with D ($D_V$, $D_F$, and $D_L$). S within this equation is defined as the stimulations being applied within the present invention. The letter with each S designates electrode sets. For example, A may be electrode set 212, B may be electrode set 214, and so forth. As shown above, each collection of electrode sets has a matrix that stays constant with a specific set of outputs R and/or D. The electrode set may then be stimulated at a specific level based on the input of the equations in order to achieve a desired motion.

Figure 8:
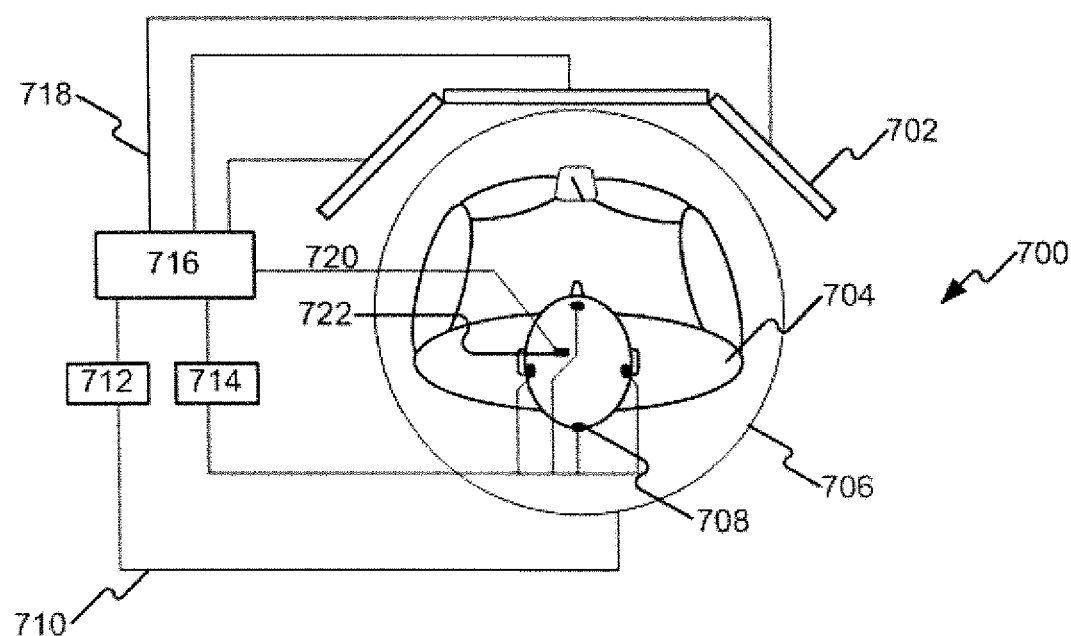
FIG. 8 is a schematic block diagram of a motion stimulation system.

FIG. 8 is a schematic block diagram of one embodiment of a motion stimulation system 700. In general, the system 700 may be used to coordinate stimulation through sets of electrodes on the human subject with visual or actual motion of the subject so as to affect the subject's perception of motion. The visual motion is motion that the subject perceives with their eyes, such as by seeing their surroundings move around them when they move, or when they are viewing a simulated environment on one or more computer-controlled display devices 702. The actual motion may be achieved by the subject 704 being on a platform, such as a moving vehicle, or a mechanically actuated platform such as in a simulator system. Thus, the system 700 may be implemented to compensate for motion in an actual system such as an airplane or other vehicle, or in a simulator system such as a videogame or full scale simulator such as a flight simulator.

Referring to particular components in FIG. 8, a human subject 704 is shown on a movable platform 706. The subject 704 has electrodes 708 attached about their body, such as around their head in the manner discussed above. The electrodes are connected to a current generator 714, which is in turn connected to a central controller 716 in the form of a digital computer such as a personal computer or a vehicle computer. In implementations where the subject 704 is provided with simulated movements by the system 700, a motion controller 712 is connected to the platform 706 by control lines 710 in order to move the platform in a desired direction at a desired speed. In addition, the computer 716 can be connected to one or more video display devices 702 via video connectors 718.

The computer 716 is a central controller for the operation of the system 700. The computer may initially receive input about motion for the subject 704, which may include actual motion or simulated motion. These inputs are received from sensors 722 placed on the human subject. Inputs may include measurements of orientation, speed, direction, observed motion, and the like. The sensors send inputs along line 720 to the computer for further computation. For example, the subject 704 may move a yoke or other controller such as a joystick (whether wired or wireless) as part of an actual or simulated operation so as to bring about a desired movement of the system. Such input may take familiar forms, either in an actual system or a simulator system. The computer 716 may compute responses to the input from the subject 704 and may display a result of the input on display devices 702, where the system 700 is a simulator system.

The computer 716 may also determine parameters that must be provided in terms of motion stimulation to the subject 704 so that the subject 704 physically perceives an appropriate amount of motion or desired motion. These parameters may be determined through stimulation software within a stimulation determination module (not shown) that may be embedded within the computer 716 and/or the current generator 714. This software may also be embedded with the various matrix equations discussed above.

For example, in a system 700 with motion platform 706 active (either by motion of the floor or induced motion), the desire may be to cancel out all or some of the actual motion of the subject 704 in the platform 706 so as to make the operation more comfortable for the subject 704. In such an environment, the desire may also be to change the subject's perceived motion to some level other than what they would otherwise perceive without intervention. In a system 700 where the motion platform 706 is active or inactive, the aim may be to provide total perceived motion that matches and is coordinated with the visual motion on the displays 702, such as in a videogame system that does not have a platform 706. Where a platform 706 is available, the aim may be to add perceived motion to the actual motion of the platform 706 so as to match the user's total perceived motion (actual plus induced perceived motion) with what they are seeing on the displays 702. The computer 716 can thus send appropriate signals to the motion controller 712 and the current generator 714 so as to move the subject 704 to the extent possible to match the visual cues provided by the displays 702, and to add stimulation to compensate and provide an appropriate non-visual total perception of motion to reach the desired goal.

Other additional or alternative features may also be provided with the system 700. For example, in addition or alternatively to providing the subject 704 with a yoke or other controller for controlling displays 702 and/or a platform 706, the subject may be provided with an input mechanism for reporting perceived motion, such as reporting a level of discomfort felt in response to receiving various stimulations. Such input may be used in studying the subject 704 to determine the subject's susceptibility to motion-related discomfort, and to determine whether GVS stimulations being provided to the subject 704 are effective or need to be adjusted. In this manner, a GVS system for cancelling motion-induced effects may be calibrated for the particular subject, and settings suggested by such calibration may then be used with respect to the subject. For example, those settings may be electronically stored, and then loaded the next time the subject appears for simulator training. Also, a portable stimulation system may be provided for people who have motion sickness, where motion sensors (e.g., accelerometers and/or gyroscopes) may be placed in the portable device and may cause stimulations to be provided to a subject to offset motion sensed by the motion sensors of an airplane or some other vehicle in which the subject is located. For example, a portable box may be mounted to the subject's belt, and a cap or headband containing stimulation electrodes may be placed over the subject's head.

Figure 9:
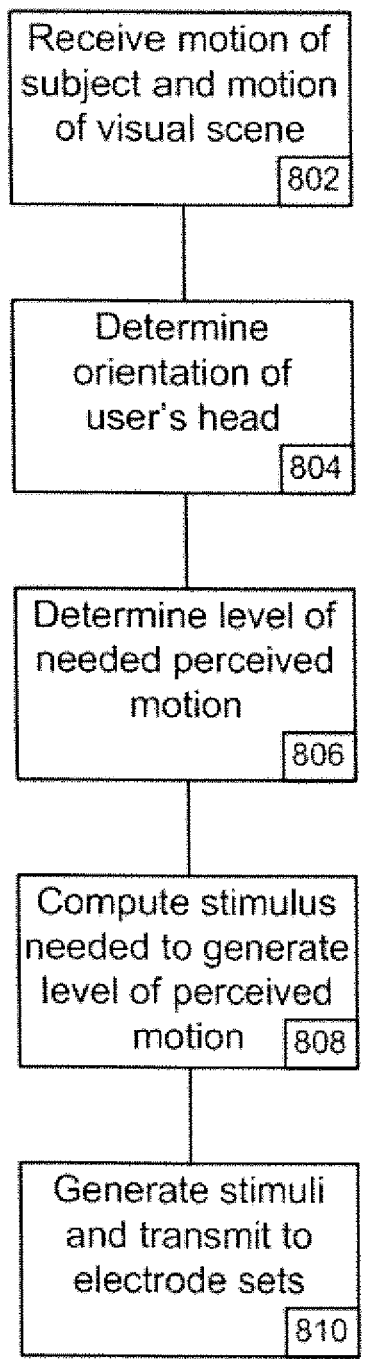
FIG. 9 is a flowchart showing a method of using motion stimulation on a subject.

FIG. 9 is a flowchart showing one embodiment of a method for using motion stimulation on a subject. In general, the process is directed to receiving inputs about an actual motion of a subject, or a motion that the subject is perceiving or is to perceive visually. In a simulator environment, such inputs will supplement any actual motion provided by the process to the user, so as to better match their non-visual perception of motion with their visual perception of motion. The process includes a step of receiving a motion of the subject and may also include a step of receiving a motion of the visual scene being displayed to the subject (802). An additional step may be receiving a control input from the user regarding desired movement in a certain direction and at a certain speed as specified by the user. Such an input, in a real system, may come from joysticks, accelerometers and/or other sensors mounted in a vehicle such as an airplane. With a simulator or other form of videogame, the input may come from a subject moving an input mechanism like a yoke or handheld controller so as to move a vehicle in which they are being simulated. Another step in the process is determining the orientation of a user's head (804). This means that the user's actual motion is determined based on the orientation of a user's head. As noted, the actual motion may come from outside the system where real activity is taking place, or may come from within the system where the process may control a platform, enclosure, chair, or other similar device in which the user has been placed on or within. In the latter situation, the movement of the platform or enclosure may be insufficient to match the user's non-visual perception of motion to the user's visual perception of motion.

The process also includes a step of determining a needed level of perceived non-visual motion (806). In a typical situation, such a determination may be made by determining the level of motion being provided visually to video displays in the system and subtracting a corresponding level of actual motion being provided to the subject by a physical platform to which the subject is connected. The orientation of the subject's head may also be accounted for. Such comparison and computation may be completed by conventional mechanisms. The computation may occur in a computer that runs the simulation or in a specialized controller directed to provide stimulations that create perceived non-visual motions in order to match perceived visual motions appropriately.

Another part of the process is the step of computing a stimulus needed to generate a level of perceived non-visual motion (808). Thus for example, during the step of determining a level of perceived motion (806), it may be determined that the user needs to be provided with a perception of rotation through 90 degrees over 1 second. It may be further determined that a platform can provide half of that perception. Thus a 45 degree input may need to be provided to the user to match their perceived non-visual motion with the perceived visual motion (e.g., provided by video monitors). The step of computing a stimulus (808) may use the techniques above to determine the level of stimulation and the stimulation profile over time that is needed to provide such perception. In certain situations, the needed perceived non-visual motion may not need to match the perceived visual motion, such as when it is impossible to match the two. In such a situation, a best practical simulated non-visual motion may be determined, and stimulation may be provided to give the subject such a perception of motion.

The process also includes a step of generating stimuli and transmitting the stimuli to the subject, such as over leads to multiple sets of electrodes placed on the subject as described above. The stimuli may take an appropriate profile such as a ramped step signal having appropriate ramp angles, as discussed above, and that profile can be repeated over time, such as over a time during which the subject's perception is to be simulated. For example, if the subject is simulating a long (e.g., several seconds) banking action in an airplane, the stimulations needed to achieve a non-visual perception of that action may be delivered repeatedly to the subject during the banking procedure in coordination with video signals that show the view out of an airplane with the occurrence of a correlated banking procedure.

Example 4

Alleviating Simulator-Related Sickness

Use of GVS in mitigation of nausea and dizziness associated with simulator sickness and motion sensitivity was tested. An entire electrode montage for the head was applied to each of 30 test subjects—with half receiving actual GVS per the equations described above, and half receiving sham stimulations (no GVS). Each subject was seated in a replica of an actual flight seat as part of a simulator, and positioned before a video display. Each subject was given the same instructions. A series of inputs designed to cause most, if not all, subjects to experience some level of stimulator sickness was then executed. For the first 5 minutes, the visual field responded as expected to the control inputs. After this initial acclimation period, the input from the throttle was automatically modified by a sinusoid at 4 Hz, with amplitude from 0.5 to 5 times the user commanded motion. For example, if the subject commanded a constant turn in yaw at 30 degrees/second, after the acclimation period, the speed of this turn would vary between 15 degrees/second to 150 degrees/second. A visual flow field (white dots on a black background) was displayed in order to eliminate subjectivity that may arise with complex visuals. The controls included a joystick (controlling pitch and roll), throttle (controlling speed), and foot pedals (controlling yaw).

Subjects were trained to move in all axes. The tests were run for a time equal to the shortest of (a) 20 minutes; (b) as long as the subject wished; and/or (c) based on a determination by the test administrator that the subject was in distress. Symptoms of simulator sickness were reported by the subject and were assessed by the test administrator on visual analog scales that ranked from 0 to 10. Symptoms included such ailments as drowsiness, pallor, vomiting, dizziness, sweats, nausea, headaches, warmth, salivation, and other related symptoms. The data was tabulated for each symptom from the visual analog scale for both self-reported and observed symptoms. The averages indicate a score of approximately 4.2 for sham subjects and 2.8 for subjects who had received actual GVS. All symptoms were scored by the subjects or test administrator on a scale from 0 to 10, with higher numbers indicating a higher severity. For example, a score of 4 was always "worse" than a score of 2. Although the highest individual score was 10, no symptom had an average score greater than 5. Based on the bar graphs in FIGS. 10A-B, there was a marked decrease in dizziness, nausea, and sweating, although there was a slight increase in drowsiness when GVS was applied. FIG. 10C pulled apart the nausea scores for all 23 subjects that were able to be recorded since this symptom is most directly relevant to simulator sickness.

Figure 10A:
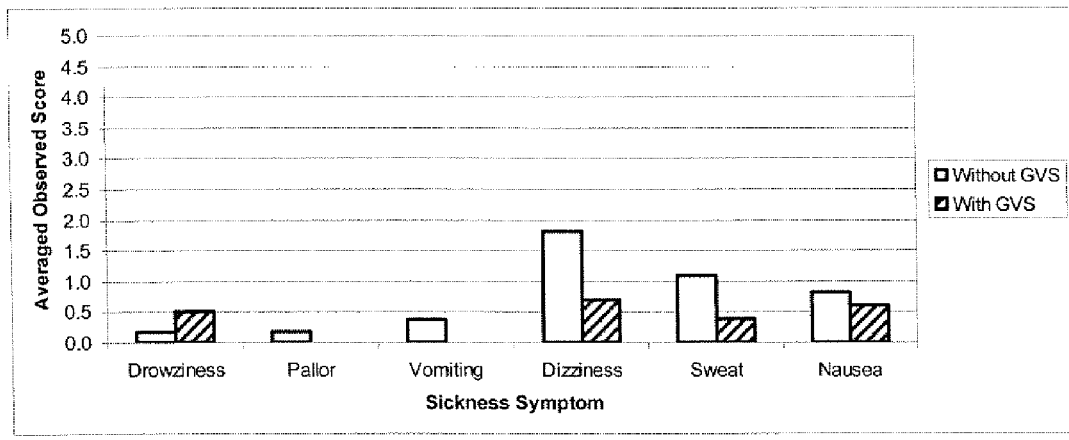
FIG. 10A is a graph of the average observed scores of sickness symptoms that resulted from simulator tests with GVS and without GVS (sham).
Figure 10B:
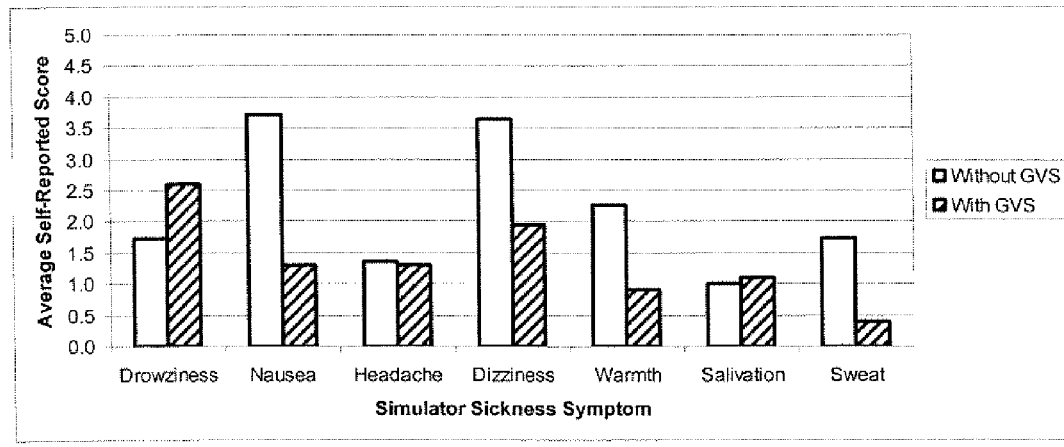
FIG. 10B is a graph of the average self-reported scores of sickness symptoms that resulted from simulator tests with GVS and without GVS (sham).
Figure 10C:
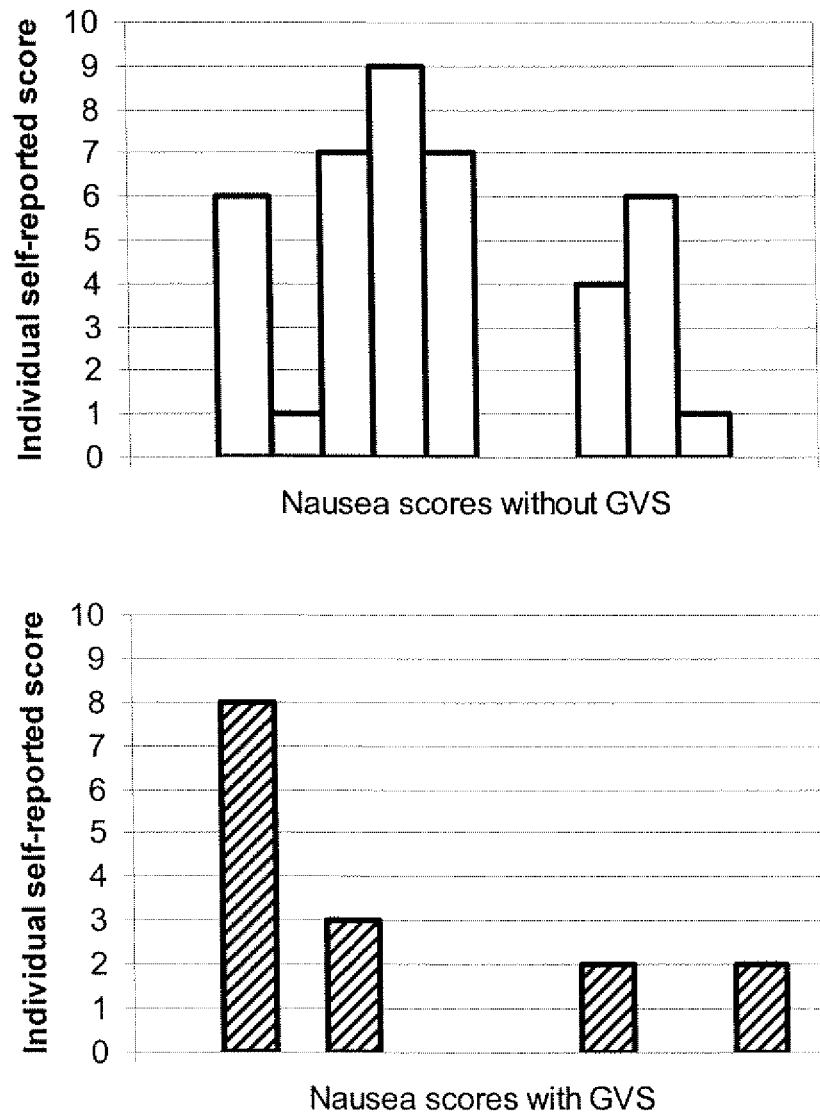
FIG. 10C is a graphical comparison of all the subjects' self reported scores regarding the symptom of nausea without GVS (sham) and with GVS.

As shown in FIGS. 10A-C, the self-reported and observed scores demonstrate a consistent pattern, with the following trends noted in using the GVS-coupled simulator: (1) marked decrease in average nausea, dizziness, sweat, and warmth, which are all symptoms of motion sickness; (2) both the incidence and severity of nausea decreased; and (3) a slight increase in drowsiness was noted. The incidence of nausea decreased from 8 of 12 sham subjects (67%) to 4 of 11 GVS subjects (36%). Moreover, when nausea was reported, the median value decreased from 6 to 2.5. Therefore, the present invention decreased both the incidence (67% to 36%) and severity (6 to 2.5) of the nausea. This means that fewer people overall were getting nauseated and the severity of nausea felt by people decreased with the GVS application.

The GVS applied in this example uses the same setup described above for the simulator. By using GVS to induce vestibular motion sensations that match the visual field, the incidence and severity of motion-related symptoms associated with the simulator were reduced.

Example 5

Computer and Electrical Components

Figure 11:
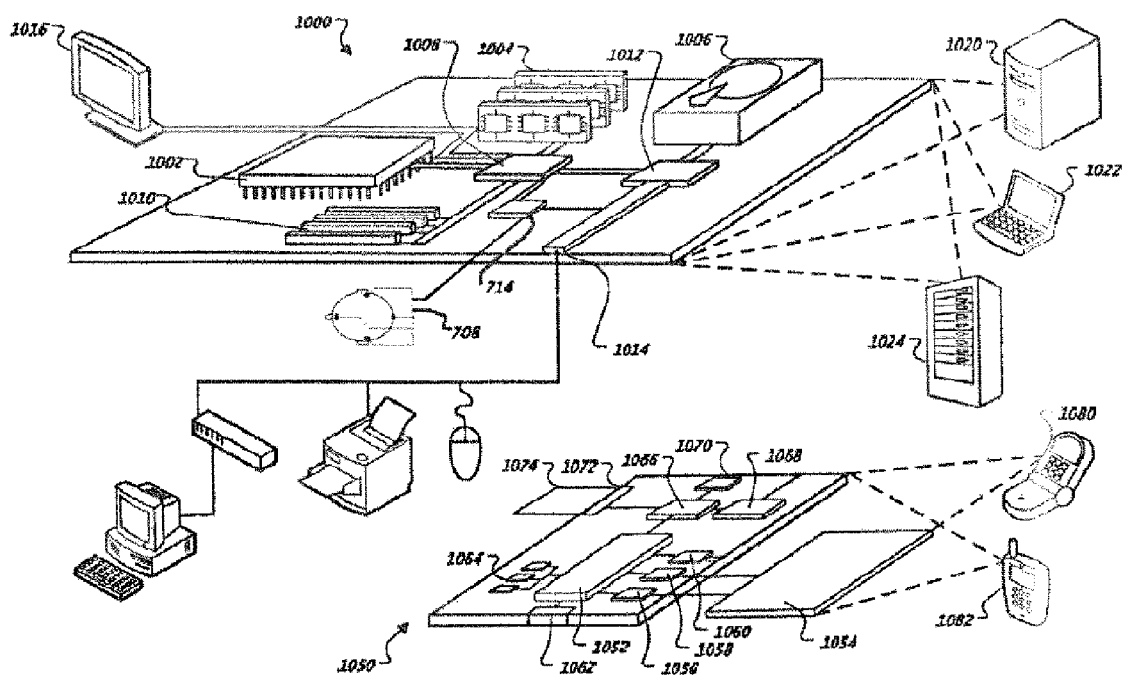
FIG. 11 is a schematic block diagram of one embodiment of the present invention including electronic components.

FIG. 11 shows one embodiment including a generic computing device 1000 and a generic mobile computer device 1050, which may be used with the techniques described herein. Computing device 1000 is intended to represent various forms of digital computers, such as laptops, desktops, workstations, personal digital assistants, servers, blade servers, mainframes, and other appropriate computers. Mobile computer device 1050 is intended to represent various forms of mobile devices, such as personal digital assistants, cellular telephones, smartphones, and other similar computing devices. As one example, computing device 1000 may be used to operate a simulation system, to receive inputs, and provide GVS stimulations coordinated with an ongoing stimulation. This system would be capable of reducing simulator sickness in a subject or match total perceived motion for a subject to a visual perception of motion that the subject is undergoing. Mobile computer device 1050 may be a portable device that can be used to provide GVS so as to reduce motion sickness, such as in a commercial airline passenger. The components shown here, their connections and relationships, and their functions, are meant to be exemplary only, and are not meant to limit implementations of the inventions described and/or claimed in this document.

Computing device 1000 includes a processor 1002, memory 1004, a storage device 1006, a high-speed interface 1008 connected to memory 1004, high-speed expansion ports 1010, and a low speed interface 1012 connected to a low speed bus 1014 and storage device 1006. Each of the components 1002, 1004, 1006, 1008, 1010, and 1012 are interconnected using various busses, and may be mounted on a common motherboard or in other manners as appropriate. The computing device 1000 may also include a stimulation generator card 714 connected directly to the low speed bus 1014 or the high speed interface 1008. The stimulation generator 714 outputs to a set of electrodes 708. The stimulation generator 714 sends a certain amount of electrical signals to the electrodes 708. The stimulation generator 714 may also include a stimulation determination module embedded within the generator card 714 or the module may be embedded within the processor 1002. This module is used for computing the amount of needed stimulation to be sent to electrodes 708 by the stimulation generator 714. The processor 1002 can process instructions (such as stimulation of electrodes) for executing within the computing device 1000, including instructions stored in the memory 1004 or on the storage device 1006 in order to display graphical information for a GUI on an external input/output device, such as display 1016 coupled to high speed interface 1008. In other implementations, multiple processors and/or multiple buses may be used, as appropriate, along with multiple memories and various types of memories. Also, multiple computing devices 1000 may be connected, with each device providing portions of the necessary operations (e.g., as a server bank, a group of blade servers, or a multi-processor system).

The memory 1004 stores information within the computing device 1000. In one implementation, the memory 1004 is a volatile memory unit or units. In another implementation, the memory 1004 is a non-volatile memory unit or units. The memory 1004 may also be another form of computer-readable medium, such as a magnetic or optical disk.

The storage device 1006 is capable of providing mass storage for the computing device 1000. In one implementation, the storage device 1006 may be or contain a computer-readable medium, such as a floppy disk device, a hard disk device, an optical disk device, a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer-readable or machine-readable medium, such as the memory 1004, the storage device 1006, memory on processor 1002, or a propagated signal.

The high speed controller 1008 manages bandwidth-intensive operations for the computing device 1000, while the low speed controller 1012 manages lower bandwidth-intensive operations. Such allocation of functions is exemplary only. In one implementation, the high-speed controller 1008 is coupled to memory 1004, display 1016 (e.g., through a graphics processor or accelerator), and to high-speed expansion ports 1010, which may accept various expansion cards (not shown). In one implementation, low-speed controller 1012 is coupled to a storage device 1006 and a low-speed expansion port 1014. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 1000 may be implemented in a number of different forms, as shown in FIG. 11. For example, it may be implemented as a standard server 1020, or in a group of such servers. It may also be implemented as part of a rack server system 1024. In addition, it may be implemented in a personal computer such as a laptop computer 1022. Alternatively, components from computing device 1000 may be combined with other components in a mobile device (not shown), such as device 1050. Each of such devices may contain one or more of computing devices 1000, 1050, and the entire system may be made up of multiple computing devices 1000, 1050 communicating with each other.

Mobile computing device 1050 includes a processor 1052, memory 1064, an input/output device 1054 such as a display and/or electrodes, a communication interface 1066, and a transceiver 1068, among other components. The device 1050 may also be provided with a storage device, such as a microdrive or other device, to provide additional storage. Each of the components 1050, 1052, 1064, 1054, 1066, and 1068, are interconnected using various buses, and several of the components may be mounted on a common motherboard or in other manners as appropriate.

The processor 1052 can execute instructions within the mobile computing device 1050, including instructions stored in the memory 1064. The processor may be implemented as a chipset of chips that include separate and multiple analog and digital processors. The processor may provide, for example, for coordination of the other components of the device 1050, such as control of user interfaces and electrodes, applications run by device 1050, and wireless communication by device 1050.

Processor 1052 may communicate with a user through control interface 1058 and display interface 1056 coupled to the input/output device 1054. The input/output device 1054 as a display may be, for example, a TFT LCD (Thin-Film-Transistor Liquid Crystal Display) or an OLED (Organic Light Emitting Diode) display, or other appropriate display technology. The display interface 1056 may comprise appropriate circuitry for driving the display 1054 to present graphical, electrical, and other information to a user. The control interface 1058 may receive commands from a user and convert them for submission to the processor 1052. This control interface 1058 may also be a stimulation generator when the input/output device 1054 is a set of electrodes. The stimulation generator sends a certain amount of electrical signals to the electrodes. There may also be a stimulation determination module embedded within the stimulator generator and/or within the processor 1052. This module is used for computing the amount of needed stimulation to be sent to electrodes. In addition, an external interface 1062 may be provided in communication with processor 1052, so as to enable near area communication of device 1050 with other devices. External interface 1062 may provide, for example, for wired communication in some implementations, or for wireless communication in other implementations, and multiple interfaces may also be used.

The memory 1064 stores information within the mobile computing device 1050. The memory 1064 can be implemented as one or more of a computer-readable medium or media, a volatile memory unit or units, or a non-volatile memory unit or units. Expansion memory 1074 may also be provided and connected to device 1050 through expansion interface 1072, which may include, for example, a SIMM (Single In Line Memory Module) card interface. Such expansion memory 1074 may provide extra storage space for device 1050, or may also store applications or other information for device 1050. Specifically, expansion memory 1074 may include instructions to carry out or supplement the processes described above, and may include secure information as well. Thus, for example, expansion memory 1074 may be provided as a security module for device 1050, and may be programmed with instructions that permit secure use of device 1050. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer-readable or machine-readable medium, such as the memory 1064, expansion memory 1074, memory on processor 1052, or a propagated signal that may be received, for example, over transceiver 1068 or external interface 1062.

Mobile computing device 1050 may communicate wirelessly through communication interface 1066, which may include digital signal processing circuitry where necessary. Communication interface 1066 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 1068. In addition, short-range communication may occur, such as using a Bluetooth, WiFi, or other such transceiver (not shown). In addition, GPS (Global Positioning System) receiver module 1070 may provide additional navigation- and location-related wireless data to device 1050, which may be used as appropriate by applications running on device 1050.

Mobile computing device 1050 may also communicate audibly using audio codec 1060, which may receive spoken information from a user and convert it to usable digital information. Audio codec 1060 may likewise generate audible sound for a user, such as through a speaker, e.g., in a handset of device 1050. Such sound may include sound from voice telephone calls, recorded sound (e.g., voice messages, music files, etc.) and may also include sound generated by applications operating on device 1050.

The mobile computing device 1050 may be implemented in a number of different forms, as shown in FIG. 11. For example, it may be implemented as a cellular telephone 1080. It may also be implemented as part of a smartphone 1082, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose. The programmable processor may be coupled to receive data and instructions from, as well as transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user. A set of electrodes in various embodiments may also be implemented as an output device. A keyboard, pointing device (e.g., a mouse or a trackball) and orientation sensors provide the means for the user to provide input to the computer. Other kinds of devices can be used to provide for interaction with a user as well; for example, feedback provided to the user can be in any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), a middleware component (e.g., an application server), or a front end component (e.g., a client computer having a graphical user interface or a Web browser through which a user can interact with an implementation of the systems and techniques described herein), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

A number of embodiments have been described. Nevertheless, it will be understood that various modifications may be made without departing from the spirit and scope of the invention. For example, much of the present invention has been described with respect to particular uses for GVS, but other applications and combinations of the above described present invention would also be addressed, as would be understood by a skilled artisan upon reviewing the description above.

In addition, the logic flows depicted in the figures do not require the particular order shown, or sequential order, in order to achieve the desirable results. In addition, other steps may be provided, or steps may be eliminated, from the described flows, and other components may be added to, or removed from, the described systems. Accordingly, other embodiments are within the scope of the following claims.

Example 6

Directional Cueing

Another embodiment of the present invention is use of GVS in providing directional cueing to an ambulatory subject. An entire electrode montage for the head was applied to the subject as described above, and inputs were given based on the dose response as determined in Example 3. Target locations were chosen at random by the test administrator and then cues were given to the subject to redirect the subject's vector towards the targets. Cues included a speed and directional component. The subject was able to move forward, turn, and stop according to the GVS inputs. This technology allows for a subject to be moved to a precise target with the use of GVS.

The directional cueing may be embodied within a computer system or mobile computer system. This system may include a computer that receives an input regarding motion of a subject. This input includes a measurement of location and movement of the subject. The measurement may further include direction and speed of the subject. The cueing system may also include a stimulation determination module that is connected to the computer for computing an amount of stimulation to be provided to the subject in order to direct the subject on a course to a specific location. The course may include a direction and speed component for each step within the entire course. The system may also include a current generator that is connected to the determination module. The generator sends electrical stimulations to the subject via electrodes in order to physically move the subject at various speeds and directions to end at the specific location. There is also a set of electrodes, preferably two distinct sets of electrodes, located on the subject for causing stimulation of the subject to move at a speed in a certain direction.

This system includes a process for providing directional cueing. The process may include a step of receiving an input that includes the direction and speed of a subject's motion. This process may also include a step of determining a course required to direct a subject to a specific location. Another step may be determining an amount of stimulation required to cause the subject to take the course to the specific location desired. The stimulation is related to input from the user as to speed and direction. There may also be another step of delivering stimulation to sets of electrodes that are contacting the subject in order to cause the subject to move in the desired direction and speed.

Other Embodiments

Other embodiments will be evident to those of skill in the art. It should be understood that the foregoing detailed description is provided for clarity only and is merely exemplary. The spirit and scope of the present invention are not limited to the above examples, but are encompassed by the following claims. The contents of all references cited herein are incorporated by reference in their entireties.

Modifications and substitutions by one of ordinary skill in the art are considered to be within the scope of the present embodiments, which are not to be limited except by the following claims.

The invention claimed is:

1. A computer-implemented method for motion stimulation or treating motion sickness, the method comprising:
   receiving an indication of a sensed motion experienced by the human subject;
   determining an activation pattern of electrical stimulation signals of differing values applied to different locations on an exterior of a head or neck of the human subject needed for non-visual motion perceived by the human subject to match the sensed motion;
   generating the activation pattern of electrical stimulation signals of differing values applied to different locations on the exterior of the head or neck of the human subject; and
   providing at least three distinct sets of electrodes responsive to said activation pattern of electrical stimulation signals of differing values applied to the different locations on the exterior of the head or neck of the human subject configured to provide the human subject with a non-visual perception of motion in at least three separate directions that are coordinated with the sensed motion.

2. The method of claim 1 wherein the at least three separate directions further comprises roll, pitch, and yaw.

3. The method of claim 1 wherein the at least three separate directions is selected from the group consisting of roll, pitch, yaw, up/down, right/left, and forward/backward.

4. The method of claim 1 further comprising providing on one or more video display devices configured to display the sensed motion experienced by the human subject.

5. The method of claim 4 wherein determining the activation pattern of electrical stimulation signals comprises identifying a level of non-visual motion to match the display corresponding to the motion on the video display devices, and identifying a level of galvanic vestibular stimulation adequate to produce a sensation substantially corresponding to a level of needed motion-related stimulation.

6. The method of claim 1 wherein the indication of sensed motion experienced by the human subject is received in response to the human subject providing an input to produce simulated motion with a sensing unit.

7. The method of claim 6 wherein the sensing unit is part of a steering assembly for a simulated vehicle.

8. The method of claim 1 wherein determining the activation pattern of electrical stimulation signals comprises identifying a level of non-visual motion to counteract simulator sickness created by the motion experienced by the human subject, and identifying a level of galvanic vestibular stimulation adequate to produce a sensation substantially corresponding to a level of needed motion-related stimulation.

9. The method of claim 1 wherein the activation pattern of electrical stimulation signals comprise DC signals of differing values applied to different locations around the subject's head.

10. The method of claim 9 wherein the DC signals of differing values comprise repeated periodic DC stimulations, wherein at least two electrodes at different locations around the subject's head receive stimulations of substantially equal amplitude.

11. The method of claim 1 wherein generating activation pattern of electrical stimulation signals to the sets of electrodes in contact with the human subject alleviates a motion-related sickness.

12. The method of claim 11 wherein the motion-related sickness is selected from the group consisting of drowsiness, pallor, vomiting, dizziness, sweat, nausea, headache, warmth, and salivation.

* * * * *